(12) United States Patent
Reeves

(10) Patent No.: US 10,960,193 B1
(45) Date of Patent: Mar. 30, 2021

(54) SWIVELING TATTOO NEEDLE

(71) Applicant: Mark A. Reeves, West Columbia, SC (US)

(72) Inventor: Mark A. Reeves, West Columbia, SC (US)

(*) Notice: Subject to any disclaimer, the term of this patent is extended or adjusted under 35 U.S.C. 154(b) by 342 days.

(21) Appl. No.: 15/898,993

(22) Filed: Feb. 19, 2018

Related U.S. Application Data

(60) Provisional application No. 62/460,146, filed on Feb. 17, 2017.

(51) Int. Cl.
  *A61M 37/00* (2006.01)
(52) U.S. Cl.
  CPC ............... *A61M 37/0076* (2013.01)
(58) Field of Classification Search
  CPC ........... A61M 37/0076; A01K 11/005; A61B 17/3417
  See application file for complete search history.

(56) References Cited

U.S. PATENT DOCUMENTS

| | | | |
|---|---|---|---|
| 4,159,659 A | 7/1979 | Nightingale | |
| 4,582,060 A | 4/1986 | Bailey | |
| 4,862,772 A | 9/1989 | Piperato | |
| 5,279,552 A * | 1/1994 | Magnet | A61M 37/0076 604/47 |
| 5,471,102 A * | 11/1995 | Becker | A61M 37/0076 310/17 |
| 5,472,449 A | 12/1995 | Chou | |
| 6,065,371 A * | 5/2000 | Yacowitz | A61M 5/20 30/362 |
| 6,505,530 B2 | 1/2003 | Adler et al. | |
| 7,380,480 B1 * | 6/2008 | Chen | A61M 37/0076 604/198 |
| 2004/0116953 A1 * | 6/2004 | Dixon | A61M 37/0076 606/186 |
| 2004/0167560 A1 | 8/2004 | Merkel | |
| 2009/0090218 A1 | 4/2009 | Jarboe et al. | |
| 2012/0123462 A1 * | 5/2012 | Lee | A61M 37/0076 606/185 |
| 2012/0265232 A1 * | 10/2012 | Surbone | A61M 37/0076 606/186 |

* cited by examiner

*Primary Examiner* — Alexander J Orkin
(74) *Attorney, Agent, or Firm* — Cramer Patent & Design, PLLC; Aaron R. Cramer

(57) ABSTRACT

A tattoo needle has a paddle secured at a point adjacent the distal end of the needle and a swivel secured to the proximal end of the needle. A stationary eyelet is secured to end of the swivel opposite the needle. A sleeve slides over the barrel, which rotates. The barrel retains the paddle of the needle, thus restricting rotating motion of the needle when the barrel is rotated.

20 Claims, 5 Drawing Sheets

SWIVELING TATTOO NEEDLE

RELATED APPLICATIONS

The present invention was first described in and claims the benefit of U.S. Provisional Application No. 62/460,146 filed Feb. 17, 2017, the entire disclosures of which are incorporated herein by reference.

FIELD OF THE INVENTION

The present invention relates generally to the field of tattoo guns and more specifically relates to rotatable tattooing needles and barrels.

BACKGROUND OF THE INVENTION

The practice of tattooing has been practiced in many cultures for centuries. Tattoos are markings applied to the skin by introducing pigments into the dermal layer through multiple punctures. Modern tattoo guns apply tattoos usually through electric motors which are attached eccentrically to a needle. The rotational motion of the motor is translated to oscillation of the needle which punctures the skin hundreds or even thousands of times. The needle carries pigments through these punctures to the dermal layer of the skin changing the pigment of the skin itself.

Many modern tattoo guns are available with numerous attachments to suit the desired effect of the tattoo. Liner needles are often comprised of a few individual needles tightly grouped together to impart a solitary line into the dermis. Shader needles are commonly comprised of several needles grouped together in a wide, flat arrangement to allow the tattoo artist to effectively shade or color in a larger area of the skin with one (1) pass. Among these two (2) basic types of needles there are hundreds of variations made to fit specific tasks and impart the desired effect of the artist. These needles are typically fixed to the tattoo gun and must be changed out when a different effect is desired.

As an artist details a tattoo they are usually incentivized to select the proper needle for the desired effect which can lead to numerous needle changes during the course of a tattoo. As the artist works through the tattoo they are often presented with awkward angles and difficult-to-reach areas which the artist and even the subject are forced to adapt to and adjust their positioning. It is no surprise that tattoos can be very painful and minimizing the amount of movement and adjustment throughout the process is critical to the completion of the tattoo. To compensate for this inconvenience, many tattoo guns come with various designs to maximize the ease-of-use and maneuverability for the user.

Some tattoo guns allow the user to adjust the positioning of the motor on the gun to allow the user to pivot the motor to a more comfortable position to increase the versatility of the gun. These guns can offer decreased weight, better maneuverability and a generally more comfortable experience for their operators. Unfortunately, these guns can also increase the risk of over penetration or "blowout" when tattooing. The operator of the gun must constantly be aware of the changes made to the positioning of the motor and compensate for the dynamic changes of the gun to ensure its effectiveness.

Furthermore, many guns offer the feature of interchangeable barrels with various sized and shaped grips. These barrels can help accommodate the area the operator is working in, providing a large stable grip with vibration dampening and wieldy manipulation. Other barrels provide precise grips which facilitate high fidelity of movement and ease-of-access to tight spaces. However, these grips can be distinct in their characteristics that they may not provide the versatility an operator may desire and can necessitate frequent changing. Other guns provide adjustment to the throw of the needle. These guns allow the user to adjust the needle to the circumstance, giving it further reach for hard-to-reach areas or shorter reach for precise movements. Again, these guns while helpful in their own right, still necessitate frequent adjustments to the gun and can alter the consistency of the tattoo making it appear uneven and erratic. A suitable solution is desired.

Various attempts have been made to solve problems found in tattoo gun art. Among these are found in: U.S. Pat. No. 8,733,211 to Snijders; U.S. Pat. No. 6,033,421 to Theiss, et al.; and U.S. Pat. No. 8,522,647 to Dixon. These prior art references are representative of tattoo guns.

None of the above inventions and patents, taken either singly or in combination, is seen to describe the invention as claimed. Thus, a need exists for a reliable rotatable tattooing needles and barrels, and to avoid the above-mentioned problems.

SUMMARY OF THE INVENTION

The principles of the present invention provide such a tattoo application system that includes a needle assembly, a barrel that retains the needle assembly, and a sleeve rotatably attached to the barrel. The needle assembly is capable of being in operable communication with a tattoo gun and the sleeve is capable of being secured to the tattoo gun. Because the barrel rotates independently of the sleeve, and the inner portion of the barrel rotates independently from the outer gripping surface of the barrel, a portion of the needle assembly that is retained in the slot does not rotate. This enables a user to rotate their hand that grips the barrel outer surface for ergonomic reasons, while maintain the tattoo gun and needle in a stable position during application of a tattoo.

It is therefore an object of the present invention to provide such a needle assembly to further include an eyelet having a first end capable of being mechanically coupled to the tattoo gun, a swivel member having a first end rotatably attached to a second end of the eyelet, and a shaft having a first end affixed to a second end of the swivel member, a paddle located on an intermediate position, and a piercing member located at an opposing second end. In certain embodiments, the eyelet second end further includes a stem extending from the eyelet and a pair of discs, each circumscribing the stem. The swivel member has a conical shape and further includes a swivel bore located at the swivel member first end and a hollow interior. The swivel member first end encompasses the pair of discs.

It is a further object of the present invention to provide such a barrel to further include a slot located within the inner channel, capable of receiving the paddle and restricting lateral movement of the paddle. In certain embodiments, the slot is located within the inner channel adjacent to the barrel second end. The barrel also includes a barrel first end extending away from a first distal end of the barrel, having a barrel first end diameter. The barrel also includes a barrel second end extending away from a second distal end of the barrel, having a barrel second end diameter. The inner channel is in environmental communication with the barrel first end and second end. The barrel first end and second end are capable of enabling the shaft to pass therethrough.

It is another object of the present invention to provide such a sleeve that also includes a sleeve first end having a sleeve first diameter coterminous with the barrel first end, and a sleeve second end having a sleeve second diameter and encompassing the barrel first diameter. The sleeve second end terminates prior to the barrel outer surface and is capable of being clamped to the tattoo gun.

In certain embodiments, the piercing member comprises three (3) tines, five (5) tines, and seven (7) tines.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
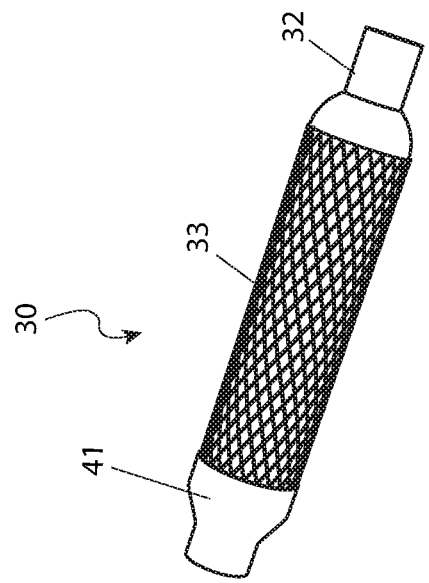
FIG. 1 is a perspective view of a swiveling tattoo needle system 10 showing the needle 20 removed from the barrel 30, according to an embodiment of the present invention.
Figure 1:
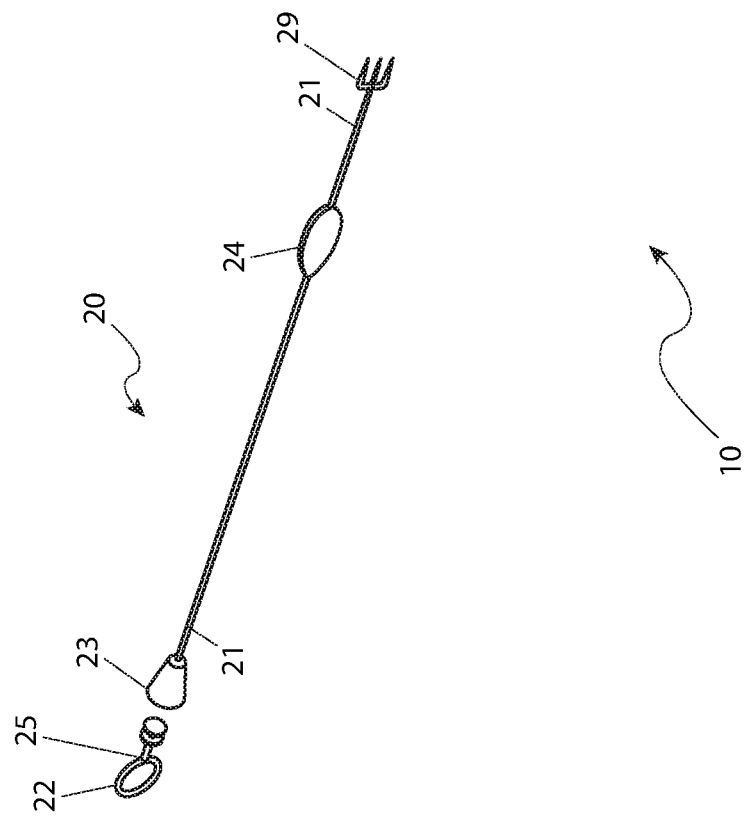

DESCRIPTIVE KEY 10 swiveling tattoo needle system
20 needle assembly
21 shaft
22 eyelet
23 swivel
24 paddle
25 stem
26 a pair of discs
27 swivel bore
29 piercing member
30 barrel
31 barrel first end
32 barrel second end
33 grip
37 first end aperture
38 second end aperture
39 first alternate piercing member
41 sleeve
42 inner channel
43 slot
49 second alternate piercing member

DETAILED DESCRIPTION OF THE PREFERRED EMBODIMENT

The present invention is directed to an accessory for a tattoo gun. In one (1) embodiment of the present invention, the swiveling tattoo needle and barrel system (herein described as the "system") 10 may comprise a barrel 30 providing a grip for a user for an attached accompanying needle assembly 20 having a swiveling component and a paddle 24. The needle assembly 20 is capable of being mechanically coupled to a tattoo gun whereas the barrel 30 acts as a grip for manipulation of the needle assembly 20 during operation.

Referring now to the drawings, there is shown in FIG. 1 a system 10 according to the preferred embodiment. The barrel 30 is shown to be generally cylindrical in its shape and can be supplied in multiple sizes and shapes. The barrel 30 has a grip 33 located on an outer surface. The grip 33 of the barrel 30 may be substantially embossed or knurled to facilitate an effective gripping surface. Extending away from opposing ends of the barrel 30 is a barrel first end 31 and a barrel second end 32, both hollow cylindrical elements integral with the barrel 30 and having a smaller diameter than the barrel 30. The barrel 30 smoothly tapers down in diameter towards both barrel first end 31 and barrel second end 32 members. An inner channel 42 of the barrel 30 is accessible through a first end aperture 37 located at the barrel first end 31 and a second end aperture 38 located at the barrel second end 32. The inner channel 42 is thusly in environmental communication with both apertures 37, 38 and also independently rotatable relative to the grip 33.

A sleeve 41 is rotatingly attached to the barrel first end 31 and has a first end coterminous with a first end of the barrel first end 31. The rotating means can be accomplished with a bearing assembly. The second end of the sleeve 41 flares outward in diameter to encompass the outer diameter of the barrel 30. In a preferred embodiment, the second end of the sleeve 41 terminates at the beginning of the grip 33. The sleeve 41 is capable of being clamped to the tattoo gun and thus provides independent rotation relative to the barrel first end 31 and hence, the barrel 30.

Further illustrated is the accompanying needle assembly 20 of the system 10. The shaft 21 is shown to be significantly longer than the barrel 30 allowing for its passage through the first end aperture 37, the inner channel 42 bored through the barrel 30, and out through the second end aperture 38.

Figure 4A:
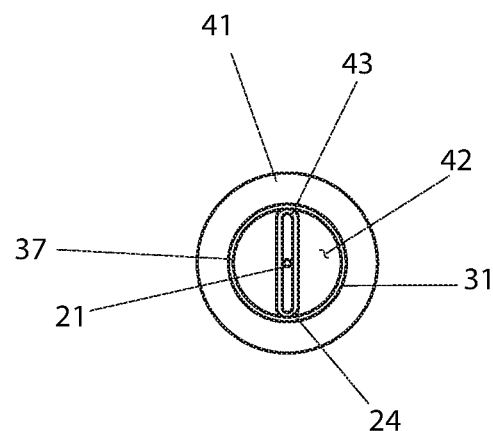
FIG. 4a is a cut-away view of the needle 20 along the line I-I of FIG. 3, illustrating the inner channel 42 and slot 43, according to a preferred embodiment of the present invention.
Figure 4B:
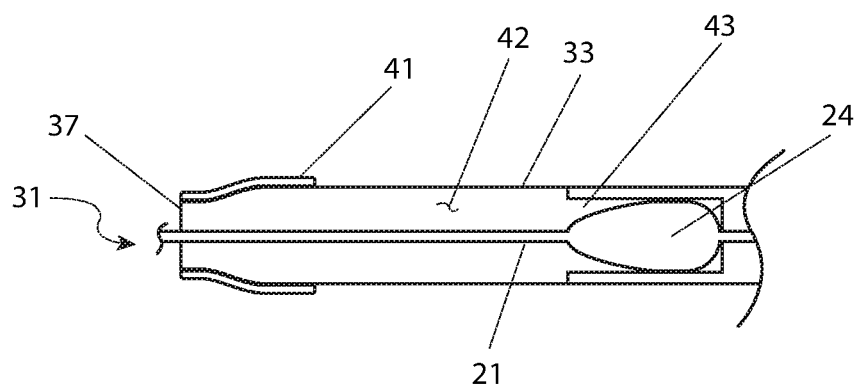
FIG. 4b is a cut-away view of the needle 20 along the line II-II of FIG. 3, illustrating the inner channel 42 and slot 43, according to a preferred embodiment of the present invention.

At the first distal end of the needle assembly 20 there is shown to be an eyelet 22 to allow its attachment to the motor of a tattoo gun. The eyelet 22 is shown to be attached to a swivel 23 which is then attached to the shaft 21 of the needle assembly 20. A more detailed description of this feature is described below. Positioned proximally on the shaft 21, towards the piercing member 29, is a paddle 24 that is a substantially flat and wide paddle portion. This paddle 24 is scaled relative to the inner diameter of the inner channel 42 in that the paddle 24 can be inserted into the first end aperture 37 of the barrel first end 31. When the needle assembly 20 is fully installed within the barrel 30, the paddle 24 resides within a slot 43 located within the inner channel 42 adjacent the barrel second end 32. As such, the inner channel 42 has a first diameter larger than a second diameter, the transition point of which resides at the slot 43. The slot 43 is shaped and sized to enable non-rotation of the paddle 24 and thus the needle assembly 20 when the barrel 30 is rotated (please see FIGS. 4a and 4b). At the opposite distal end of the needle assembly 20 there is illustrated the piercing member 29 integral with the end of the shaft 21. The piercing member 29 is shown in the illustrated embodiment to be of a flat, three-tined configuration. It should be noted that the configuration of the needle assembly 20 is flexible to the desired configuration of the user. When the needle assembly 20 is fully inserted in the inner channel 42, the piercing member 29 extends away from the barrel second end 32, preferably at a minimum distance (such as one-eighth of an inch (½ in.)).

Figure 2:
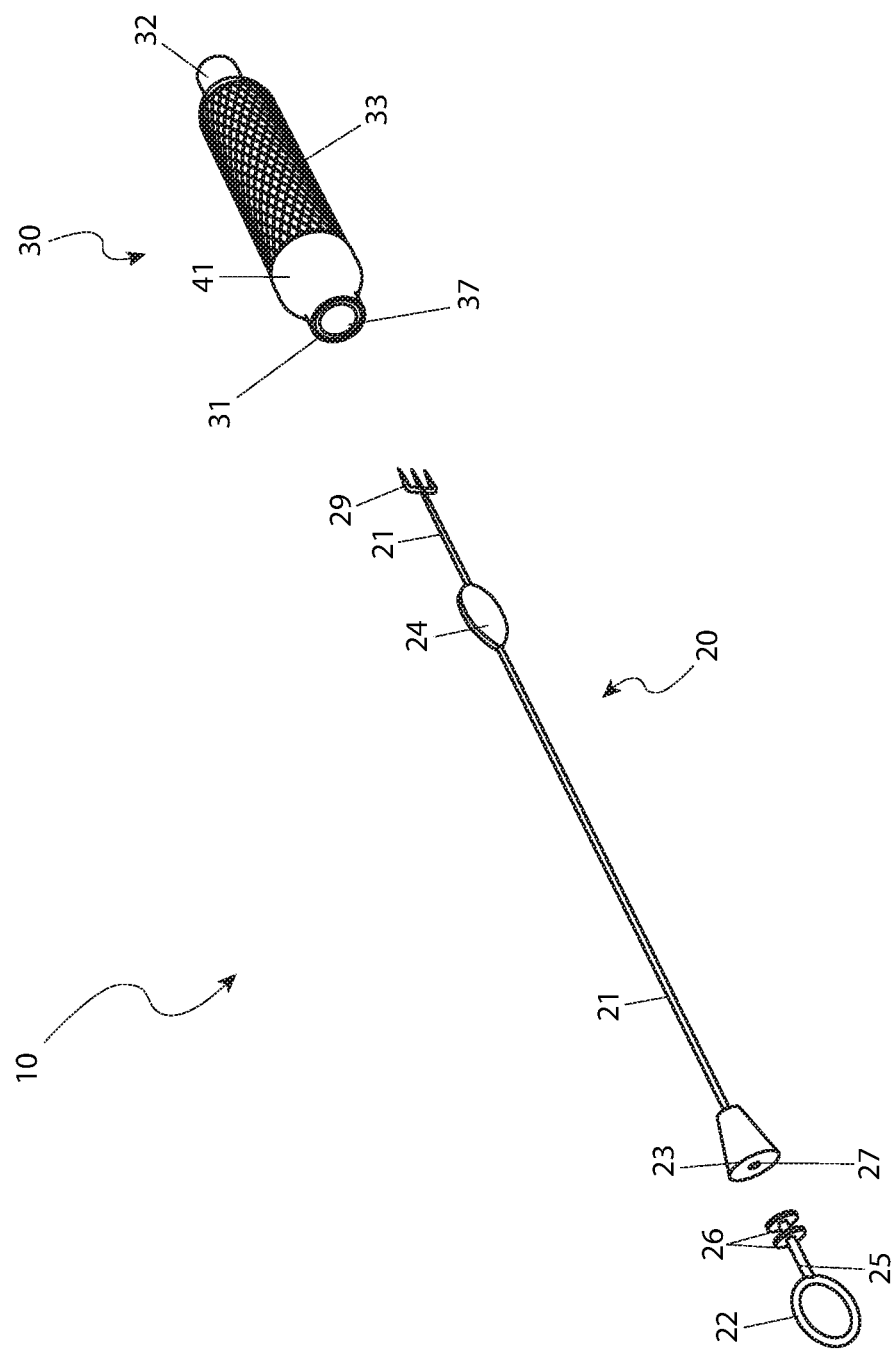
FIG. 2 is an exploded perspective view of a swiveling tattoo needle system 10 showing the needle 20 removed from the barrel 30, according to an embodiment of the present invention.

Referring now to FIG. 2 showing a top perspective view of the system 10. The drawing effectively illustrates the first end aperture 37. The first end aperture 37 is of a sufficient size to allow the paddle 24 and shaft 21 of the needle assembly 20 to extend through the barrel 30 and facilitate a mating relationship with the paddle 24 within a slot 43 (see FIGS. 4a and 4b). When the paddle 24 is inserted into the slot, a coaxial relationship between the needle assembly 20 and the barrel 30 of the system 10 is achieved. When the barrel 30 is rotated, the paddle 24 within the slot 43 stabilizes the needle assembly 20.

Referring back to FIG. 1, the swivel 23 is attached to the terminal end of the shaft 21 opposite of the piercing member 29 and is conically-shaped with the larger diameter opposite the shaft 21. The eyelet 22 has a stem 25 extending from the plane provided by the eyelet 22. At the distal end of the stem 25 there is provided a first one (1) of a pair of discs 26 which the stem 25 extends through the center thereof. The stem 25 terminates at its connection to the center of a second one (1) of the pair of discs 26. The pair of discs 26 are sized and manufactured integrally to the stem 25 and provide a swiveling means against the inner surface of the swivel 23 of the shaft 21. The stem 25 passes through the swivel bore 27 centrally located with the swivel 23 providing access to its interior. The swivel bore 27 is sized to permit the passage of the stem 25 but restricts the passage of the pair of discs 26. As such, the eyelet 22, the stem 25, and the pair of discs 26 portion of the needle assembly 20 can be integrally constructed with the swivel 23 portion of the shaft 21. The eyelet 22 is capable of being connected to the motor of a tattoo gun and effectively translates the reciprocating movement of the motor to the shaft 21 and the piercing member 29.

Figure 3:
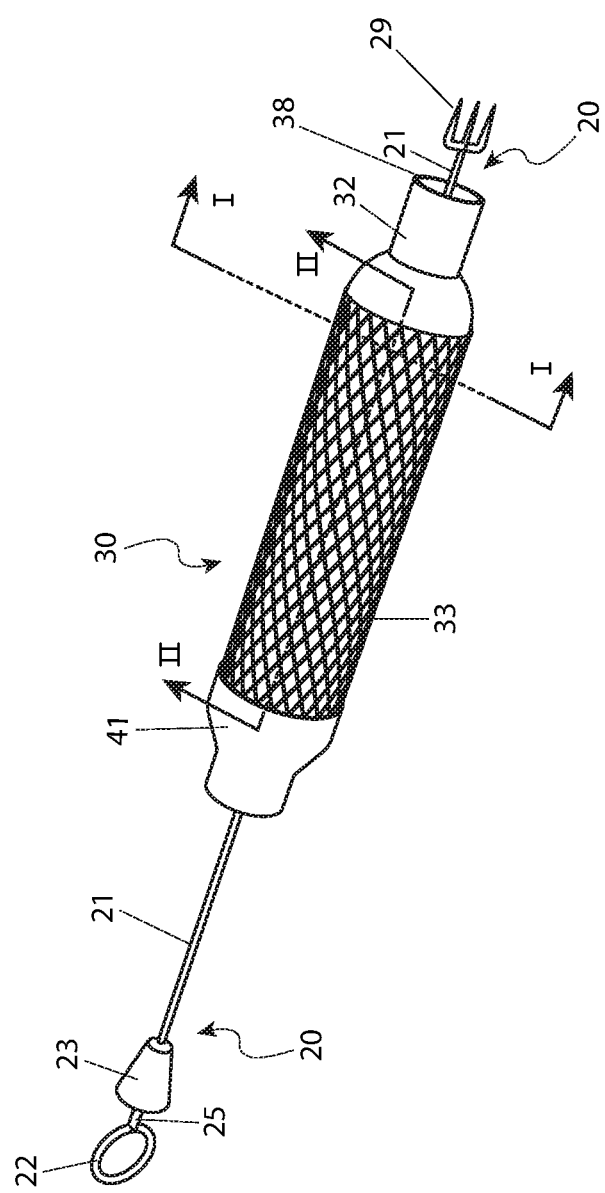
FIG. 3 is a perspective view illustrating the fully attached swiveling tattoo needle system 10 according to an embodiment of the present invention.

Referring now to FIG. 3, the system 10 is shown with its essential components configured in functional relationship with each other. The shaft 21 of the needle assembly 20 can be seen as extending through the barrel 30. The shaft 21 is shown to extend substantially beyond the barrel first end 31 allowing for its connection to a tattoo gun motor and is shown to extend substantially beyond the barrel second end 32 to enable the piercing member 29 to come into contact with the dermis of the subject of the tattoo. The paddle 24 is shown to be contained within a slot 43 (see FIGS. 4a and 4b) of the barrel 30. This relationship allows for the barrel 30 to rotate independently of needle assembly 20, and tattoo gun. The swivel 23 enables the positioning of the piercing member 29 to be manipulated without affecting the transfer of motion from the reciprocating motor of the tattoo gun to the needle assembly 20. The barrel 30 can move independently of the needle assembly 20 and tattoo gun, thereby enabling a tattoo gun operator to better manipulate the gun and needle assembly 20 along different planes and positions to provide enhanced comfort and accuracy during tattoo sessions of extended periods of time.

Figure 5:
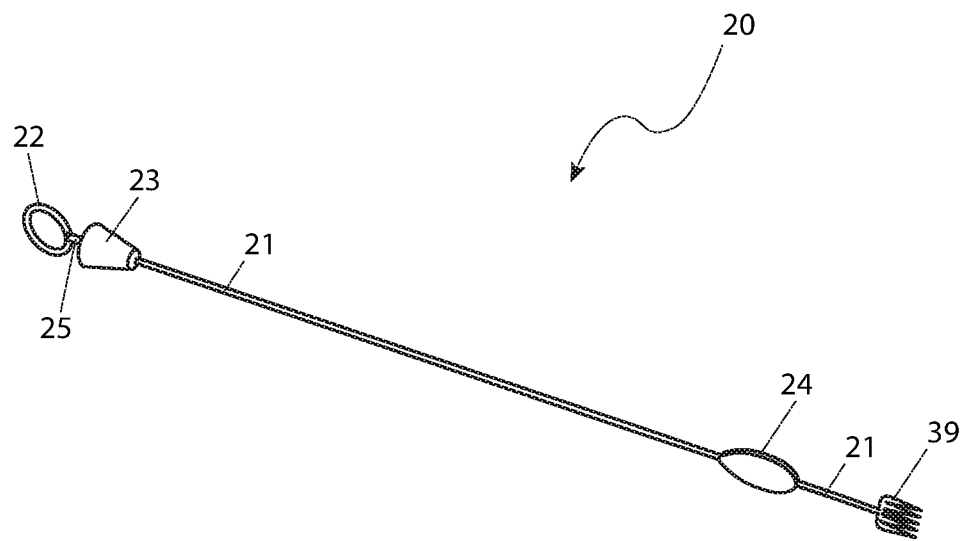
FIG. 5 is a perspective view of the needle 20 having a first alternate piercing member 39, according to an alternate embodiment of the present invention; and, FIG. 6 is a perspective view of the needle 20 having a second alternate piercing member 49, according to another alternate embodiment of the present invention.
Figure 6:
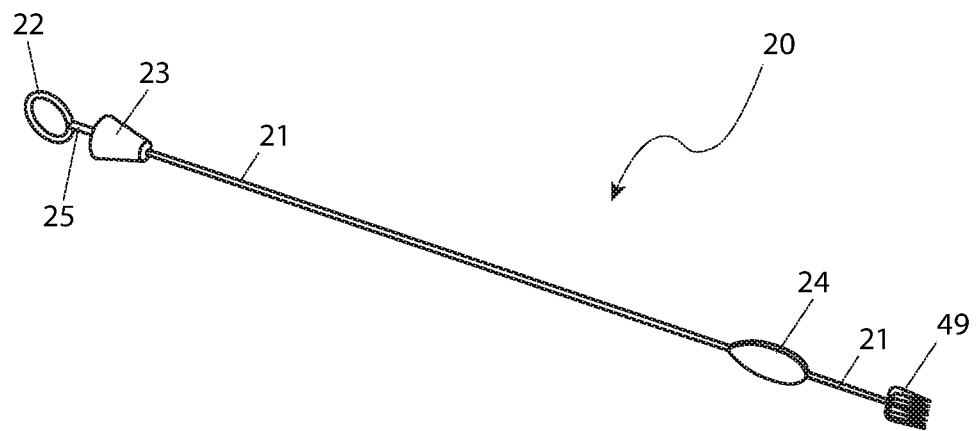

Referring now to FIGS. 5 and 6, it is generally accepted that a multitude of needle assemblies 20 may be necessary for the completion of a tattoo and the needle component 20 of the system 10 may be adapted to any of the necessary variations. The needle assemblies 20 may be manufactured with the essential unique components to allow for their use with the system 10. Certain needle assemblies 20 may have piercing members 39, 49 having a differing number of tines, such as five (5) tines or even seven (7) tines.

The exact specifications, materials used, and method of use of the system 10 may vary upon manufacturing.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. A tattoo application system, comprising:
    a needle assembly, comprising:
        an eyelet having a first end capable of being mechanically coupled to a tattoo gun;
        a swivel member having a first end rotatably attached to a second end of said eyelet; and
        a shaft having a first end affixed to a second end of said swivel member, a paddle located on an intermediate position, and a piercing member located at an opposing second end;
    a barrel, comprising:
        an outer surface having a barrel center diameter;
        an inner channel independently rotatable relative to said outer surface;
        a slot located therewithin said inner channel receiving said paddle and restricting lateral movement of said paddle;
        a barrel first end portion extending distally from a proximal end of said barrel, having a barrel first portion diameter; and
        a barrel second end portion extending away proximally from a distal end of said barrel, having a barrel second portion diameter; and
    a sleeve rotatably attached to said barrel first end portion, having:
        a sleeve first end having a sleeve first diameter coterminous with said barrel first end portion; and
        a sleeve second end having a sleeve second diameter, said sleeve second end encompassing said barrel first portion diameter, said sleeve second diameter larger than said sleeve first diameter, said sleeve second end capable of being clamped to said tattoo gun;
    wherein said inner channel is in environmental communication with said barrel first end portion and said barrel second end portion; and
    wherein said barrel first end portion and said barrel second end portion are enabling said shaft to pass therethrough.

2. The system of claim 1, wherein said eyelet second end further comprises a stem extending from said eyelet and a pair of discs, said eyelet and said pair of discs each circumscribing said stem.

3. The system of claim 2, wherein said swivel member has a conical shape and further comprises:
    a swivel bore located at said swivel member first end; and
    a hollow interior;
    wherein a swivel first end diameter at said swivel member first end is larger than a swivel second end diameter and said swivel member second end.

4. The system of claim 3, wherein said piercing member comprises three tines.

5. The system of claim 3, wherein said piercing member comprises five tines.

6. The system of claim 3, wherein said piercing member comprises seven tines.

7. The system of claim 1, wherein said sleeve second end terminates prior to said barrel outer surface.

8. The system of claim 1, wherein said slot is located adjacent said barrel second end portion.

9. The system of claim 1, wherein said swivel member first end encompasses said pair of discs.

10. A tattoo application system, comprising:
   a needle assembly, comprising:
   an eyelet having a first end capable of being mechanically coupled to a tattoo gun;
   a swivel member having a first end rotatably attached to a second end of said eyelet; and
   a shaft having a first end affixed to a second end of said swivel member, a paddle located on an intermediate position, and a piercing member located at an opposing second end;
   a barrel, comprising:
      a grip located on an outer surface having a barrel center diameter;
      an inner channel independently rotatable relative to said grip;
      a slot located therewithin said inner channel, receiving said paddle and restricting lateral movement of said paddle;
      a barrel first end portion extending distally from a proximal end of said barrel, having a barrel first portion diameter; and
      a barrel second end portion extending away proximally from a distal end of said barrel, having a barrel second portion diameter; and
   a sleeve rotatably attached to said barrel first end portion, having:
      a sleeve first end having a sleeve first diameter coterminous with said barrel first end portion; and
      a sleeve second end having a sleeve second diameter, said sleeve second end encompassing said barrel first portion diameter, said sleeve second diameter larger than said sleeve first diameter, said sleeve second end capable of being clamped to said tattoo gun;
   wherein said inner channel is in environmental communication with said barrel first end portion end and said barrel second end portion; and
   wherein said barrel first end portion and said barrel second end portion are enabling said shaft to pass therethrough.

11. The system of claim 10, wherein said eyelet second end further comprises a stem extending from said eyelet and a pair of discs, said eyelet and said pair of discs each circumscribing said stem.

12. The system of claim 11, wherein said swivel member has a conical shape and further comprises:
   a swivel bore located at said swivel member first end; and
   a hollow interior;
   wherein a swivel first end diameter at said swivel member first end is larger than a swivel second end diameter and said swivel member second end.

13. The system of claim 12, wherein said piercing member comprises three tines.

14. The system of claim 12, wherein said piercing member comprises five tines.

15. The system of claim 12, wherein said piercing member comprises seven tines.

16. The system of claim 10, wherein said sleeve second end terminates prior to said barrel outer surface.

17. The system of claim 10, wherein said slot is located adjacent said barrel second end portion.

18. The system of claim 10, wherein said grip is embossed on said outer surface.

19. The system of claim 10, wherein said grip comprises a knurled portion of said outer surface.

20. The system of claim 10, wherein said swivel member first end encompasses said pair of discs.

* * * * *